United States Patent [19]

Sawyer et al.

[11] 4,329,290

[45] May 11, 1982

[54] ANTITHROMBOTIC DERIVATIVES OF AMMONIUM ASCORBATE

[76] Inventors: Philip N. Sawyer, 7600 Ridge Blvd., Brooklyn, N.Y. 11209; Leon D. Freeman, 48 Alta Way, Corte Madera, Calif. 94925

[21] Appl. No.: 117,066

[22] Filed: Jan. 31, 1980

Related U.S. Application Data

[63] Continuation-in-part of Ser. No. 35,637, May 3, 1979, abandoned, which is a continuation of Ser. No. 701,874, Jul. 1, 1976, Pat. No. 4,164,585.

[51] Int. Cl.$^3$ ............................................. C07D 307/62
[52] U.S. Cl. ................................................... 549/316
[58] Field of Search ....................................... 260/343.7

[56] References Cited

PUBLICATIONS

Felice et al., Chem. Abst. vol. 49, 1949, 7100b.
Chem. Abst. Subject Index 1955, 307s, central col.
Runti, Chem. Abst. 14273A, 1955.
Runti, II Farmco-Ed. Sc. vol. X, p. 424.

Primary Examiner—Jane T. Fan
Attorney, Agent, or Firm—Posnack, Roberts, Cohen & Spiecens

[57] ABSTRACT

A solution of L-ascorbic acid and a solution of para amino benzoic acid are mixed and the mixture evaporated to permit recovery of a solid compound. The compound is administered to a host to reduce thrombotic tendencies.

1 Claim, 1 Drawing Figure

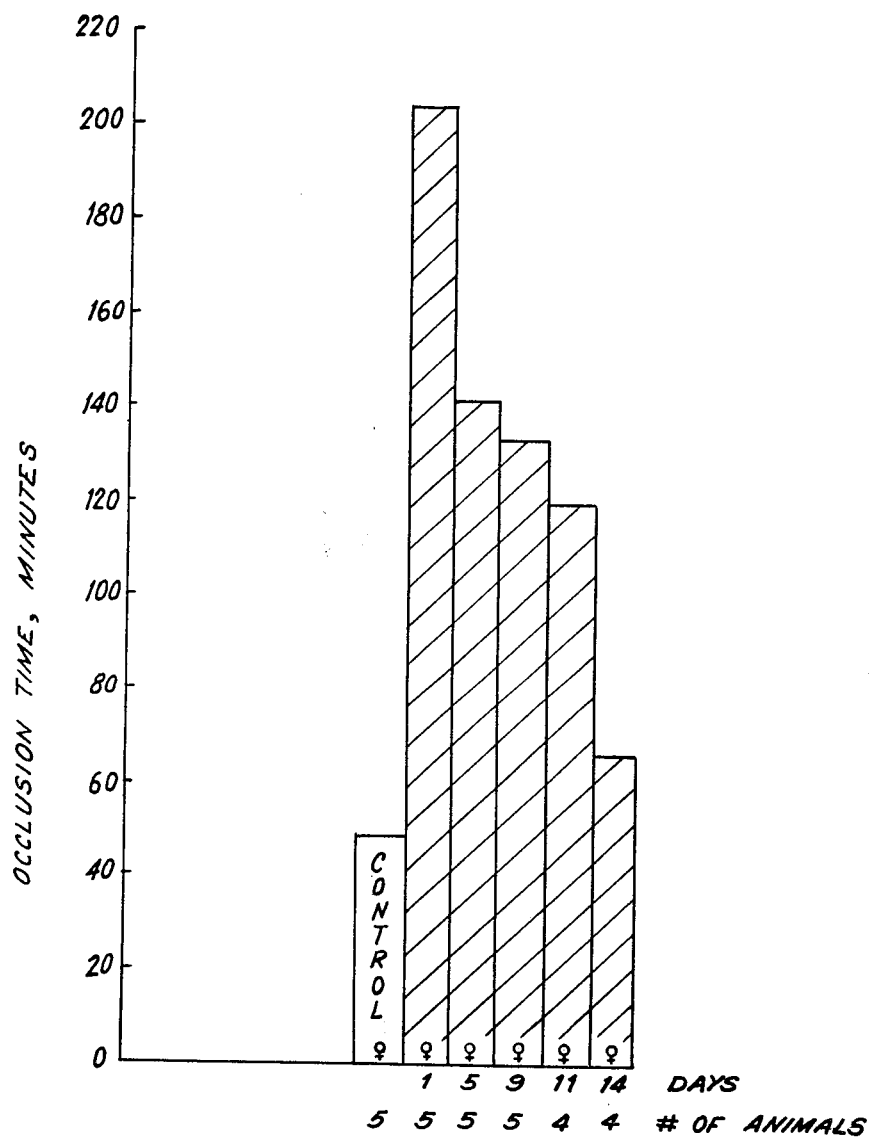

ANTITHROMBOTIC DERIVATIVES OF AMMONIUM ASCORBATE

OTHER APPLICATIONS

This application is a continuation-in-part of our earlier filed application Ser. No. 35,637, filed May 3, 1979 now abandoned, which is a continuation of application Ser. No. 701,874 filed July 1, 1976 (now U.S. Pat. No. 4,164,585).

FIELD OF INVENTION

This invention relates to compounds of organic acids and to methods of making and using the same particularly for pharmaceutical purposes.

BACKGROUND OF THE INVENTION

U.S. Pat. No. 3,722,504 describes a screen for testing pharmaceutical compounds based at least partly on their ability to increase the negative surface charge of the vascular system. U.S. Pat. No. 3,722,504, by way of example, discloses a pharmaceutical compound which prevents thrombosis by modifying the intimal surface charge of the vascular system.

Para amino benzoic acid increases the net negative surface charge of blood vessels and blood cells. It produces marked increases in the current induced occlusion time in rat mesentary vessels (see U.S. Pat. No. 3,956,504). It produces no measurable effect on blood coagulation studies. It has a limited effect on blood vessel wall pores as shown by electro-osmotic studies.

Para amino benzoic acid, further, has good antithrombotic characteristics but tends to have relative little anti-coagulant activity as shown by its lack of effect on the coagulation studies including partial thromboplastin time, thrombin time and recalcification time. It is therefore a very useful antithrombotic drug.

Para amino benzoic acid has various very significant properties as a drug:
1. It is inexpensive;
2. It is known to be non-toxic in humans;
3. It can be used for long periods of time without significant incidence of pathological manifestations.
4. The material can be taken orally in large dosages without significant toxicity.

In man, dosages have been administered, for example, as high as 12 to 24 grams a day without significant side effects. It has furthermore been used for a large number of diseases in man including the therapy of Ricketsial diseases before the development of anti-biotics, for tuberculosis in very large dosage and in the treatment of certain protozoan diseases and other infestation. It has long been thought to be a mild anti-inflammatory agent.

In humans with arteriosclerotic peripheral vascular disease, para amino benzoic acid has been shown to increase blood flow in ischemic limbs as measured by Barcroft plethysmographic studies and Doppler blood flow measurements. Studies which were carried out in approximately fifty patients resulted in an approximate doubling of blood flows in patients in which para amino benzoic acid salt was effective. U.S. Pat. No. 3,956,504 has been issued on the effect of para amino benzoic acid on blood flow in man.

The long term effects of vitamin C on scurvy in man is a primary event of historical interest in medicine. The effects of vitamin C to prevent scurvy are extraordinarily well documented throughout the world. Man, deprived of vitamin C for periods longer than approximately sixty days, starts to display evidence of capillary fragility and bleeding into all tissues and organs. Vitamin C has the following characteristics:

1. It is a co-enzyme in the Kreb's cycle.
2. It is a reducing agent and electron donor in all known biological systems.

L-ascorbic acid or vitamin C has a variety of biological functions some of which are not completely understood (Zitent et al. 1964). Large doses of L-ascorbic acid appear to have value in prevention and symptom reduction in the common cold and other viral diseases (Linus Pauling 1974). Recent experimental evidence indicates that L-ascorbic acid is effective in reducing serum cholesterol levels. C. Spittle (The Lancet, July 28, 1973; pp. 199–201 and Dec. 11, 1971; pp. 1280–1281) suggested that dosages of 1 to 2 grams of vitamin C per day can be beneficial in the prevention of deep vein thrombosis as well as in reducing the incidence of atherosclerotic complications in man. Recent research indicates that ascorbic acid may reduce the incidence of myocardial infarction (Knox, E. G., The Lancet, pp. 1465, June 30, 1973). L-ascorbic acid, further, appears to offset the thrombogenic effects of oral contraceptives as demonstrated by prolongation of occlusion times in the mesenteric vessels.

Good results were obtained in a pilot study using seven volunteer subjects to determine the effects of ascorbic acid on (1) plasma coagulation characteristics (2) serum cholesterol levels (3) platelet aggregability and (4) surface charge characteristics of red cells and platelets. Vitamin C in these subjects was shown to decrease platelet aggregability and increase the electrophoretic mobility of all the tested cells.

There has been little evidence to indicate that vitamin C effects measured blood coagulability as demonstrated by partial thromboplastin time, thrombin times and thrombin recalcification times.

Spittle et al. have tested vitamin C in a randomized group of patients with thrombophlebitis. The protective effect of vitamin C against thrombosis has been shown by a randomized double-blind trial using patients who were shown to be prone to deep-venous thrombosis. In a total of fifty-three patients, it was observed that the incidence of deep venous thrombosis was 33% in patients dosed with L-ascorbic acid compared to 60% in the placebo group (Spittle, C. R., The Lancet, pp. 199, July 28, 1973). The dose given was 1 gram per day. This correlation between the intake of vitamin C and reduction in the number of thrombotic episodes has been confirmed by other sources. In burn patients, where it is customary to use large doses of vitamin C to speed healing, there has been an apparent demand for treatment of deep-vein thrombosis. This information is based on the experience of one hospital over a five and one-half year period during which time 159 patients over forty years of age were treated with large doses of vitamin C (Spittle, C. R. "The Action of Vitamin C on Blood Vessels," Amer. Heart J. 88:387, 1974).

A combination of para amino benzoic acid and vitamin C has been shown, for example, in Runti, Il Farmaco, Ed. Sci., Vol. X, 1955, pp. 424–431.

SUMMARY OF THE INVENTION

It is an object of the invention to provide an improved combination of para amino benzoic acid and L-ascorbic acid.

It is another object of the invention to provide an improved pharmaceutical compound having improved utility for extended periods following administration.

Yet another object of the invention is to provide improved methods for the treatment of hosts and the prevention of vascular conditions.

Still another object is to promote the development of useful compounds based on organic acids and the like.

A further object of the invention is to provide new methods for the development of pharmaceutical compounds.

To achieve the above and other objects of the invention, there is provided a method comprising reducing thrombotic tendencies in a host by administering to the host a compound derived from two organic acids.

According to one embodiment of the invention, one of the acids is L-ascorbic acid and the other is para amino benzoic acid.

The compound which is derived may be a salt or ester and this compound may be administered in a dosage of 1–100 mg./kg. of body weight. The dosage is preferably administered orally, although it can be administered interperitoneally.

The compound may be formed by mixing solutions of L-ascorbic acid and various forms of para amino benzoic acid and recovering the thusly resulting solid.

The invention includes, as one aspect thereof, compounds prepared according to the above method or specifically salts and esters of L-ascorbic acid and para amino benzoic acid to obtain:

A. p-carboethoxy phenyl amino ascorbate the salt of ascorbic acid and ethyl p-amino benzoate p-CARBOETHOXY PHENYL AMMONIUM ASCORBATE B. p-glyceryl carboxy phenyl amino ascorbate the salt of ascorbic acid and glyceryl para amino benzoic acid p-GLYCERYLCARBOXY PHENYL AMMONIUM ASCORBATE C. esters of para amino benzoic acid and ascorbic acid 6 MONO-ESTER - p-AMINO BENZOYL 6- ASCORBATE 5 MONO-ESTER - p-AMINOBENZOYL 5- ASCORBATE (c) DI
(d) MONO
(e) DI
(f) TRI

BRIEF DESCRIPTION OF DRAWING

The sole FIGURE of the drawing is a chart demonstrating the prolonged activity of dosages of the compound of the invention.

DETAILED DESCRIPTION

Hereinabove, reference had been made to para amino benzoic acid. The formula for this organic acid is as follows:

Reference has also been made to L-ascorbic acid or vitamin C, the formula for which is:

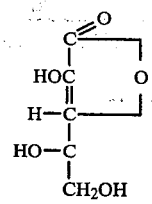

The present invention relates to compounds derived from these organic acids, namely, salts, esters and amides thereof, the synthesization of the same and the applicability thereof to the treatment of the vascular system, notably in rats, dogs and human hosts requiring such treatment.

The formula for the salt of our earlier U.S. Pat. No. 4,164,585 is as follows:

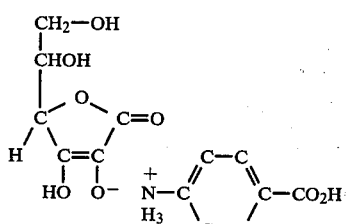

p-CARBOXY PHENYL AMMONIUM ASCORBATE

The original approach was to prepare a salt of ascorbic acid with para amino benzoic acid. Such a salt can be shown in two forms—one using the open form of ascorbic acid, the other using the enol form.

Two manufacturing procedures used are described below. Because of the ease of oxidation of ascorbic acid, it is essential to perform all operations under nitrogen and free of water and air. In one case, substantial darkening of the product resulted. It was believed this was due to the presence of moisture.

EXAMPLE I

1. A solution of para mino benzoic acid in a mixture of 50% acetone and 50% methanol was prepared with gentle heating. The concentration was approximately 100 grams per liter.

2. A similar solution was prepared with L-ascorbic acid.

3. The two solutions were mixed. Water was excluded to the extent possible.

4. The mixture was evaporated under vacuum, with nitrogen being utilized to flush the system. As the material concentrated, crystals began to appear.

5. When the solution was evaporated, until it was a thick slurry, the material was filtered through a coarse filter paper and allowed to drain as dry as possible. The surface was blanketed with nitrogen, with great care to exclude all filtered water.

6. The resultant solid was dried under high vacuum at room temperature. The ratio of L-ascorbic acid to para amino benzoic acid used was one to one on a molar basis.

EXAMPLE II

1. An alternative method of preparation used was to evaporate the solvent with careful exclusion of water and air to the point where a solid semi-dry cake was obtained in the container in which the evaporation was conducted.

2. This moist cake was then transferred to an appropriate container and dried under high vacuum. All operations are protected against exposure to air and moisture.

Other solvent systems will undoubtedly work. The above were used largely as a matter of convenience. An odor develops in the process which is removed with high vacuum drying, but must represent a by-product which is formed during the process. It must also be volatile, since it can be removed.

The first salt shown above, theoretically, only requires the removal of a molecule of water to form the amide. In general, this does not happen too readily. The distillation of the solvents may help pull off water.

Initial studies were directed toward determining the toxicity of the above-indicated compound in mammalia.

A very high dosage per kilogram of body weight in rats and dogs has been shown essentially non-toxic.

The new compound was next tested to determine its effect on rat-mesentery occlusion studies. Half lives of para amino benzoic acid have been shown to approximate one day. Half lives of vitamin C approximate 12 hours to a maximum of 1 day. The half lives of the new compound have been shown to approximate 4 to 5 days with a tail. A single dose lasts approximately 14 days. Mechanical mixing of para amino benzoic acid and L-ascorbic acid have been shown to have a maximal tail of approximately 5 to 6 days indicating by direct logic that the new compound is biologically different from the two components mixing together mechanically. Specifically, the compound derived appears to be more potent than the starting materials mixed together in a 50/50 ratio. If the agents are mixed together in the same ratio as used when making the new compound, the mechanical mixture is still not as potent as the compound derived.

The new compound has been evaluated in rat-mesentery studies. In the rat-mesentery, the new compound has been shown to prolong coagulation 3 to 4 times the normal rat-mesentery thrombosis time. The result is dramatic and prolonged since the effect of a single dose appears to extend out to 14 days before rat-mesentery occlusion times return to a normal level. This result is based on 26 rats.

Blood cells of male dogs fed with the new compound display an increase in negative surface charge which increases sequentially from the third day to approximately the 14th day, so that at 14 days there is a doubling of electrophoretic mobility over the effects seen on the fifth, sixth and seventh day.

The available evidence suggests that, as with most normal pharmacologic agents, the new compound will not produce super normality. It will, however, return toward normal any grossly abnormal measurements concerning the electrokinetic characteristics of blood cells and blood vessels in dogs.

The available evidence indicates that the new compound derived from L-ascorbic acid and para amino benzoic acid is a rather potent anti-thrombotic agent. Its effect is cumulatively greater than the effect of either of its components even when they are mechanically mixed together and given orally to rats and/or dogs. The compound is an elegant example of an electron donor compound which is useful in treating the vascular system.

The following are some results of tests comparing the new compound with a mixture of the starting materials and with the starting materials individually:

TABLE I

| MATERIAL | Dosages - Oral Route RANGE MGS/KG/DAY Minimum | Maximum | DURATION ADMINISTRATION | TOXICITY | EFFECT |
|---|---|---|---|---|---|
| PABA (X) | 1 | 10 | Indefinite | Low cutaneous manifestation. | Relatively limited |
| L-Ascorbic Acid (Y) | 0.25 mgs. | 10 | Indefinite | Low cutaneous manifestation. Gastritis. Some evidence disturbence gene pool in massive dosage. Catalytic oxidizer Krebs cycle essential vitamins. | Critical in maintenance of tissue integrity particularly vascular tree |
| X + Y (mixture) | 1 | 100mg/kg rats | Unknown long term | Very low gastritis in one rat, in high dosage 1mg/gm body weight dosage. | Prolonged rat mesentery occlusion time. Single dose run (day 1): 170 ± 20 min. Tail - 7 days. |
| X − Y (compound) | 2 | 100mg/kg | May be given long term | Very low gastritis. | Prolonged. Longer tail than X + Y Tail - 14 days Occlusion time: 206 = 24 min. |

X − Y tail - minimum 14 days in experimental animals
X + Y tail - minimum 7 days in experimental animals The following additional data was obtained relative to the utility of the new compound:

EFFECT OF NEW COMPOUND ON ELECTRICALLY INDUCED THROMBOSIS IN RAT MESENTERIC VESSELS

SINGLE LOADING DOSE
20mg/100g B.W.          MALE
MELTING POINT - 147° C.

1 DAY AFTER SINGLE LOADING DOSE
1 Rat     The occlusion time was 240 minutes

3 DAYS AFTER SINGLE LOADING DOSE
1 Rat     The occlusion time was 150 minutes
2 Rat     The occlusion time was 195 minutes The following data relates to rat-mensentery occlusion time:

RAT-MESENTERY OCCLUSION TIME

| | OCCLUSION TIME | CONTROL |
|---|---|---|
| PABA | | |
| 35 mg p.o./d × 3 d (F) | 95 min (1F) | 45 + 5 min (3F) |
| 35 mg p.o./d × 3 d (M) | 53 ± 13 min (7M) | |
| L-ASCORBIC ACID | | |
| 10mg/100g body weight/ per day × 3 days (F) | 112 ± 18 min (5F) | 45 ± 5 min (2F) |
| 10mg/100g body weight/ per day × 3 days (M) | 135 ± 14 min (2M) | 38 ± 10 min (3M) |
| PABA + L-ASCORBIC ACID | | |
| 35 mg + 10mg/100g body weight | 108 ± 23.0 min (6F) | 45 ± min (2F) |
| | 128 ± 18.0 min (2M) | 38 ± 10 min (3M) |
| 10 mg + 10 mg | 160 min (2F) | 50 minutes (1F) |
| (3M + 3F) | 175 min (3M) AF + 3M | 55 minutes (1M) |
| PABA − | | |

RAT-MESENTERY OCCLUSION TIME

| | OCCLUSION TIME | CONTROL |
|---|---|---|
| L-ASCORBIC ACID SALT (NEW COMPOUND) | | |
| 20 mgs/100 grams | 1 day after Single Loading Dose 240 min (1F) 3 days after Single Loading Dose 150 min (1M) 195 min (2F) | |

The following data relates to the occlusion time tail in female rats:

| (X − Y) - NEW COMPOUND - SINGLE DOSE/P.O. 100mg/100g body weight | Average Occluding Time |
|---|---|
| 1 day | 206 ± 24.0 min (5F) |
| 5 days | 143 ± 9.5 min (5F) |
| 9 days | 137 ± 12.0 min (5F) |
| 11 days | 127 ± 34.0 min (4F) |
| 14 days | 67 ± 4.5 min (4F) |
| | Control - 48 ± 1.1 min (5F) |

Below are tabulated some physical characteristics of batches of the compound which were made:

| | MELTING POINT | SOLUBILITY |
|---|---|---|
| Batch 1 | 157° C. | Sparingly Soluble; 1gm/100cc. $H_2O$ |
| Batch 2 | 157° C. | Same |
| Batch 3 | 147° C. | Same |

Referring next to the sole FIGURE of the drawing, it is seen that there are illustrated the effects of a single loading dose on a number of rats. A control is provided in the form of five animals and it is noted from the chart in the drawing that the control provides a rat-mesentery occlusion time relative to electrically-induced thrombosis which is, at the outset, less than a single loading dose of the new compound after 14 days.

More particularly, it will be noted that five animals were sacrificed after one day following administration of the new compound, five animals were sacrificed after five days, five more animals were sacrificed after nine days, four additional animals were sacrificed after 11 days and finally, four animals were sacrificed after 14 days. The occlusion time (in minutes) after the first day is markedly greater than that of the controls. After five days, the occlusion time is reduced but is still more than double that of the controls. Similarly, after nine days, the occlusion time is substantially greater than the controls and has reduced only very slightly from the fifth day measurements. Similarly, after 11 days, there is very little reduction in occlusion time which is still at least twice as great as that of the controls. After 14 days, measurement of four sacrificed animals still reveals an occlusion time which is greater than that of the controls.

The measurements in the drawing are based upon an administration of the compound in a dosage of 100 mg/100 g of body weight and single loading doses are employed for both the controls and the animals to which the new compound has been administered. This shows a substantial tail inures to the benefit of administration of the new compound and this is important with respect to the treatment of humans wherein oral administration of the new compound is expected to lead to a scheduled administration which provides for spaced-oral dosages over a period of days, such as, for example, one oral administration per week.

The following additional compounds have been made for the above utility:

EXAMPLE III

An antithrombotic compound is prepared in the form of the salt of glyceryl p-aminobenzoate and ascorbic acid. The structure is:

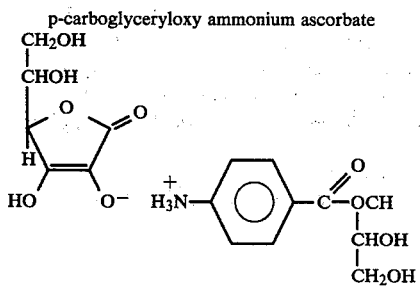

Method of Preparation

This salt was prepared by dispersing equal molar portions of the two substances in a mixture of methanol and acetone. The mixture is heated until everything is in true solution. The solvent is then evaporated until precipitation begins. At that point the mixture is chilled. The salt which crystalizes out is then collected and dried in vacuum. The characteristics of the molecule are as follows:

Melting point—117°-152° C. (broad range probably reflects salt tendency to decompose rather than give a clean melting point).

The NMR and IR curves of the salt appear to be different from the NMR and IR curves of the individual components, indicating a new molecule is present.

EXAMPLE IV

An antithrombotic compound is prepared in the form of the salt of ethyl p-aminobenzoate and ascorbic acid. The structure is:

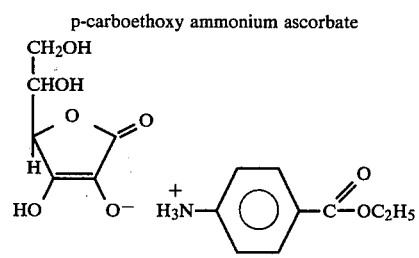

Method of Preparation

The method is identical to that for the ethyl p-aminobenzoate salt.

Melting point—88°-168° C. (broad range reflects salt decomposition).

The IR and NMR analyses show unique spectral differences from the component compounds.

EXAMPLE V

An antithrombotic compound is prepared in the form of esters of p-aminobenzoic acid with ascorbic acid. A mixture of esters consisting of more than one of the following structures has been prepared. IR and NMR data have been obtained to show the presence of ester bonding. Thin layer chromatography shows the presence of more than one component. The structures for esters are:

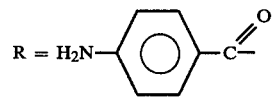

MONO-ESTERS:

(1)        (2)

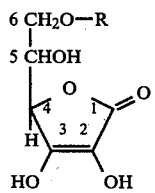 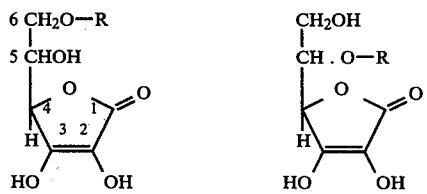

6-MONO ESTER      5-MONO ESTER

-continued (3) 2-MONO ESTER 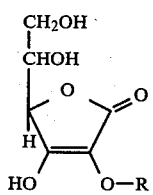

(4) 3-MONO ESTER 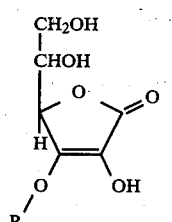

DI-ESTERS:

(5) 5,6 di-ester 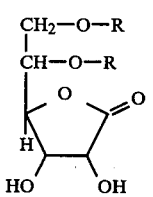

(6) 2,6 di-ester 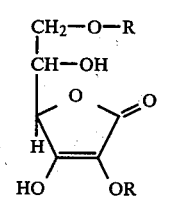

(7) 2,5 di-ester 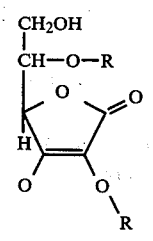

(8) 3,6 di-ester 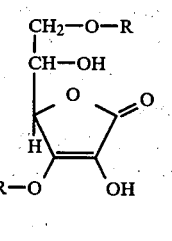

(9) 3,5 di-ester 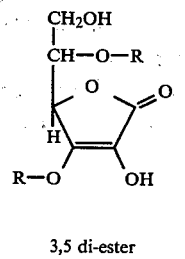

(10) 2,3 di-ester 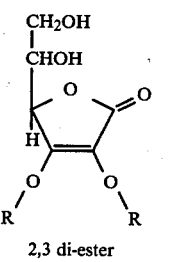

TRI-ESTERS:

(11) 3,5,6-tri-ester 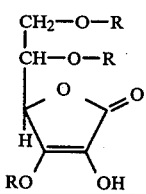

(12) 2,5,6 tri-ester 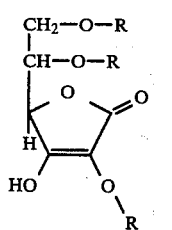

(13) 2,3,6 tri-ester 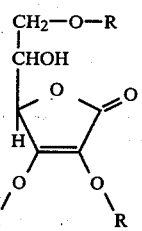

(14) 2,3,5 tri-ester 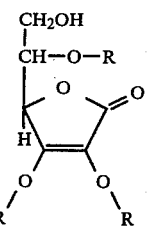

TETRA-ESTERS:

(15) tetra-ester 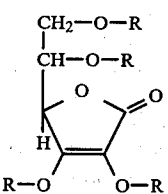

Method of Preparation

The esters were prepared by reacting p-nitrobenzoyl chloride with ascorbic acid in a solvent with a basic component chloride acceptor present, such as pyridine or triethanolamine. By reacting these materials under reflux conditions, esterfication occurs with the release of hydrochloric acid, as shown in the following schema.

p-nitrobenzoyl chloride + ascorbic acid
    mono-ester (s) + HCl
    di-ester(s) + HCl
    tri-ester + 3 HCl After the isolation by evaporation of the solvents, the nitroesters are reacted with suitable reducing agents, which will only reduce the nitro group. These include zinc and hydrochloric acid and lithium aluminum borohydride. Other reducing agents could be used.

The new compounds were isolated by evaporation of the solvent. Removal of all color was accomplished by treatment of the solvent solution with activated carbon. The product is a mixture of some or all of the esters of p-aminobenzoic acid with ascorbic acid.

There will now be obvious to those skilled in the art, many modifications and variations of the above methods and compounds. These modifications and variations will not depart from the scope of the invention if defined by the following claims or if generally equivalent thereto.

What is claimed is:

1. P-carboglyceryloxy ammonium ascorbate:

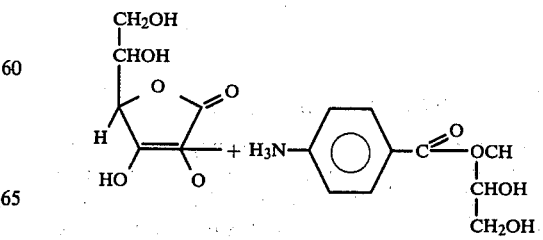

* * * * *